United States Patent [19]

Deraney

[11] Patent Number: 6,017,596
[45] Date of Patent: Jan. 25, 2000

[54] KIT AND METHOD FOR PRODUCING SCENT EMITTING ARTIFICIAL FLOWER TYPE ARTICLES

[76] Inventor: Germaine A. Deraney, 240 Main St. #320, Marlboro, Mass. 01752-3856

[21] Appl. No.: 09/082,681

[22] Filed: May 21, 1998

[51] Int. Cl.⁷ ........................................................ A01N 3/00
[52] U.S. Cl. ................................ 428/27; 428/24; 428/905
[58] Field of Search .................................. 428/24, 905, 27, 428/26, 4; D11/117; D21/496

[56] References Cited

U.S. PATENT DOCUMENTS 5,609,928   3/1997   Yedlin et al. .

*Primary Examiner*—Deborah Jones
*Assistant Examiner*—Wendy Boss

[57] ABSTRACT

A new kit and method for producing scent emitting artificial flower type articles. The inventive device includes an elongate first stem member and an elongate second stem member that is insertable into the first stem member. A first fringe member has an attachment portion at one end and a plurality of strips that extend from the other end to the attachment portion. A second fringe member has a plurality of first strips and second strips that each extend from a respective end of the second fringe member towards an attachment portion that is positioned between the ends of the second fringe member. A plurality of leaf members each have a leaf-shaped portion that extends from an elongate attachment portion. A third fringe member has an attachment portion at one end and a plurality of strips that extend from the other end towards the attachment portion. A porous strip receives scent emitting liquid. A scent emitting liquid may also be provided.

10 Claims, 3 Drawing Sheets

KIT AND METHOD FOR PRODUCING SCENT EMITTING ARTIFICIAL FLOWER TYPE ARTICLES

BACKGROUND OF THE INVENTION

1. Field of the Invention

The present invention relates to artificial flower-type articles and more particularly pertains to a new kit and method for producing scent emitting artificial flower type articles.

2. Description of the Prior Art

The use of artificial flower-type articles is known in the prior art. More specifically, artificial flower-type articles heretofore devised and utilized are known to consist basically of familiar, expected and obvious structural configurations, notwithstanding the myriad of designs encompassed by the crowded prior art which have been developed for the fulfillment of countless objectives and requirements.

Known prior art artificial flower-type articles include U.S. Pat. No. 5,282,572; U.S. Pat. No. 5,077,102; U.S. Pat. No. 4,958,768; U.S. Pat. No. 4,171,754; U.S. Pat. No. 4,919,981; and U.S. Pat. No. Des. 315,321.

While these devices fulfill their respective, particular objectives and requirements, the aforementioned patents do not disclose a new kit and method for producing scent emitting artificial flower type articles. The inventive device includes an elongate first stem member and an elongate second stem member that is insertable into the first stem member. A first fringe member has an attachment portion at one end and a plurality of strips that extend from the other end to the attachment portion. A second fringe member has a plurality of first strips and second strips that each extend from a respective end of the second fringe member towards an attachment portion that is positioned between the ends of the second fringe member. A plurality of leaf members each have a leaf-shaped portion that extends from an elongate attachment portion. A third fringe member has an attachment portion at one end and a plurality of strips that extend from the other end towards the attachment portion. A porous strip receives scent emitting liquid. A scent emitting liquid may also be provided.

In these respects, the kit and method for producing scent emitting artificial flower type articles according to the present invention substantially departs from the conventional concepts and designs of the prior art, and in so doing provides an apparatus primarily developed for the purpose of producing scent emitting artificial flower type articles.

SUMMARY OF THE INVENTION

In view of the foregoing disadvantages inherent in the known types of artificial flower-type articles now present in the prior art, the present invention provides a new kit and method construction wherein the same can be utilized for producing scent emitting artificial flower type articles.

The general purpose of the present invention, which will be described subsequently in greater detail, is to provide a new kit and method for producing scent emitting artificial flower type articles apparatus and method which has many of the advantages of the artificial flower-type articles mentioned heretofore and many novel features that result in a new kit and method for producing scent emitting artificial flower type articles which is not anticipated, rendered obvious, suggested, or even implied by any of the prior art artificial flower-type articles, either alone or in any combination thereof.

To attain this, the present invention generally comprises an elongate first stem member and an elongate second stem member that is insertable into the first stem member. A first fringe member has an attachment portion at one end and a plurality of strips that extend from the other end to the attachment portion. A second fringe member has a plurality of first strips and second strips that each extend from a respective end of the second fringe member towards an attachment portion that is positioned between the ends of the second fringe member. A plurality of leaf members each have a leaf-shaped portion that extends from an elongate attachment portion. A third fringe member has an attachment portion at one end and a plurality of strips that extend from the other end towards the attachment portion. A porous strip receives scent emitting liquid. A scent emitting liquid may also be provided.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new kit and method for producing scent emitting artificial flower type articles apparatus and method which has many of the advantages of the artificial flower-type articles mentioned heretofore and many novel features that result in a new kit and method for producing scent emitting artificial flower type articles which is not anticipated, rendered obvious, suggested, or even implied by any of the prior art artificial flower-type articles, either alone or in any combination thereof.

It is another object of the present invention to provide a new kit and method for producing scent emitting artificial flower type articles which may be easily and efficiently manufactured and marketed.

It is a further object of the present invention to provide a new kit and method for producing scent emitting artificial flower type articles which is of a durable and reliable construction.

An even further object of the present invention is to provide a new kit and method for producing scent emitting artificial flower type articles which is susceptible of a low cost of manufacture with regard to both materials and labor, and which accordingly is then susceptible of low prices of sale to the consuming public, thereby making such kit and method for producing scent emitting artificial flower type articles economically available to the buying public.

Still yet another object of the present invention is to provide a new kit and method for producing scent emitting artificial flower type articles which provides in the apparatuses and methods of the prior art some of the advantages thereof, while simultaneously overcoming some of the disadvantages normally associated therewith.

Still another object of the present invention is to provide a new kit and method for producing scent emitting artificial flower type articles that is highly ornamental and easy to transport and handle.

Yet another object of the present invention is to provide a new kit and method for producing scent emitting artificial flower type articles which includes an elongate first stem member and an elongate second stem member that is insertable into the first stem member. A first fringe member has an attachment portion at one end and a plurality of strips that extend from the other end to the attachment portion. A second fringe member has a plurality of first strips and second strips that each extend from a respective end of the second fringe member towards an attachment portion that is positioned between the ends of the second fringe member. A plurality of leaf members each have a leaf-shaped portion that extends from an elongate attachment portion. A third fringe member has an attachment portion at one end and a plurality of strips that extend from the other end towards the attachment portion. A porous strip receives scent emitting liquid. A scent emitting liquid may also be provided.

Still yet another object of the present invention is to provide a new kit and method for producing scent emitting artificial flower type articles that has a scent strip coupled to a removable second stem member such that the scent strip can be exchanged when a different scent is desired.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
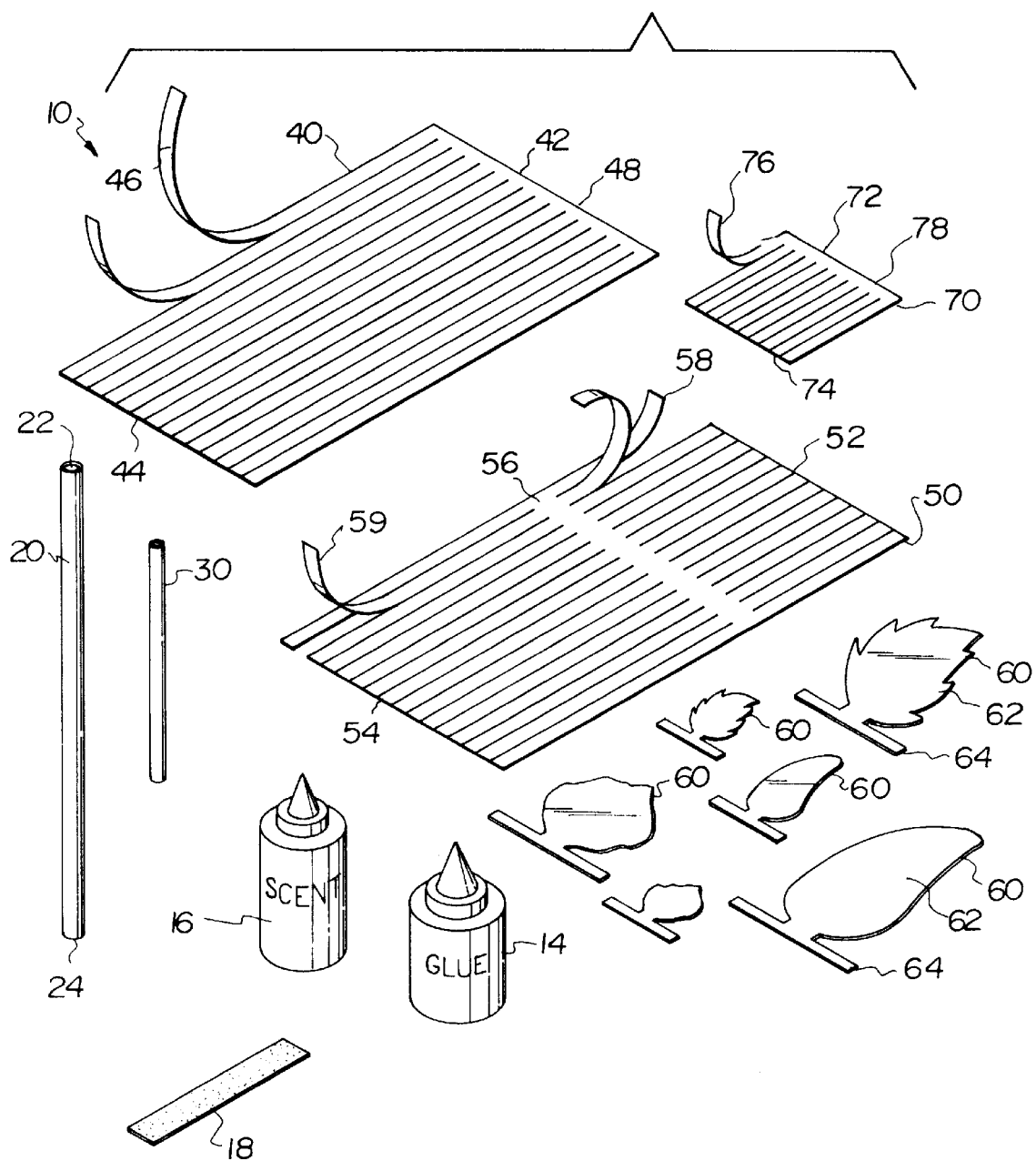
FIG. 1 is a schematic view of a new kit and method for producing scent emitting artificial flower type articles according to the present invention.

With reference now to the drawings, and in particular to FIGS. 1 through 7 thereof, a new kit and method for producing scent emitting artificial flower type articles embodying the principles and concepts of the present invention and generally designated by the reference numeral 10 will be described.

As best illustrated in FIGS. 1 through 7, the kit for producing scent emitting artificial flower type articles 10 comprises an elongate first stem member 20 and an elongate second stem member 30 that is insertable into the first stem member 20. A first fringe member 40 has a plurality of strips 46 that extend from a second end 44 towards a first end 42. A second fringe member 50 has a plurality of first strips 58 and second strips 59 that each extend from a respective end 52,54 of the second fringe member 50 towards an attachment portion 56 that is positioned between the ends 52,54 of the second fringe member 50. A plurality of leaf members 60 each have a leaf-shaped portion 62 that extends from an elongate attachment portion 64. A third fringe member 70 has a plurality of strips 76 that extend from a second end 74 towards a first end 72. A scent emitting liquid 16 and a porous strip 18 for receiving the scent emitting liquid 16 are also provided.

Figure 2:
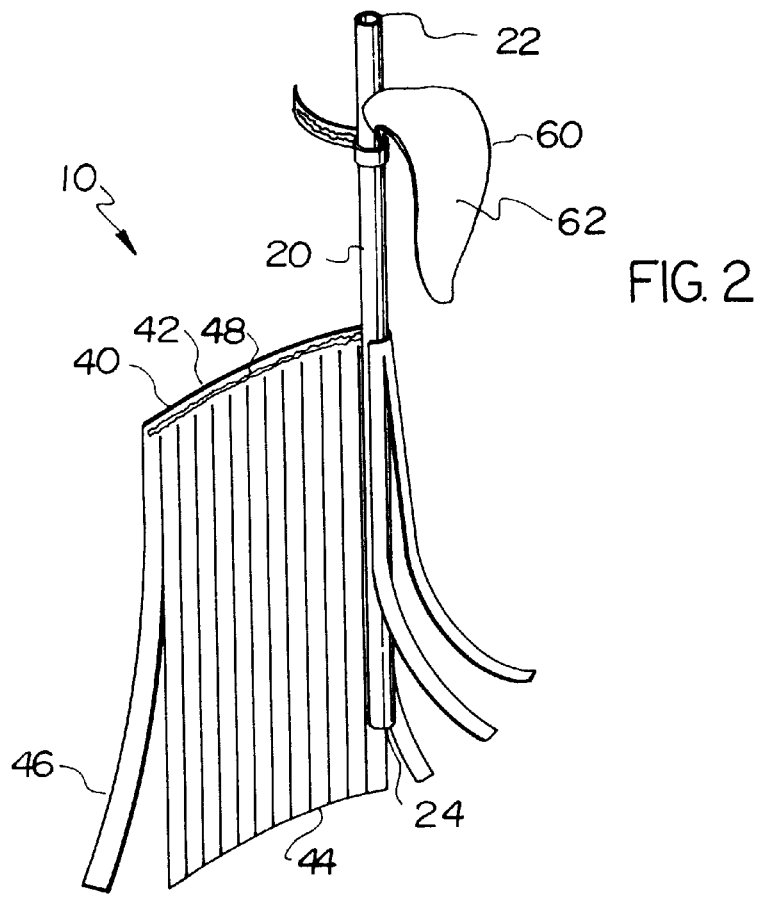
FIG. 2 is a perspective view of the present invention particularly illustrating wrapping of a fringe member and a leaf member around a stem member.
Figure 3:
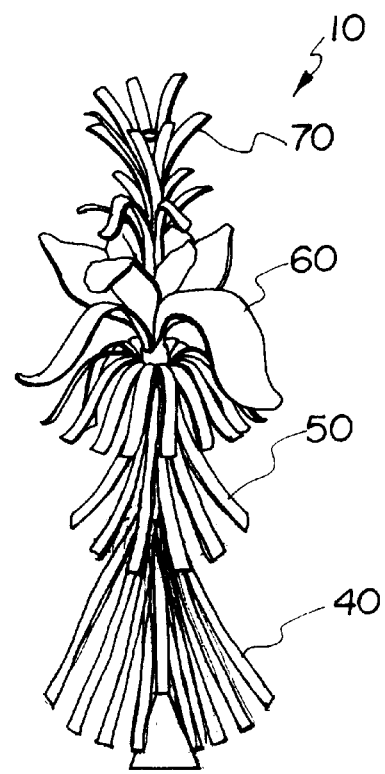
FIG. 3 is a perspective view of the present invention illustrating a completed scent emitting artificial flower type article.
Figure 4:
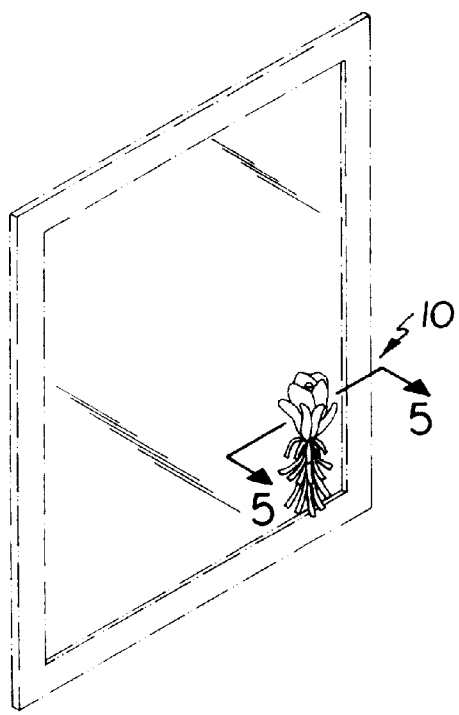
FIG. 4 is a perspective view of the present invention in use.
Figure 5:
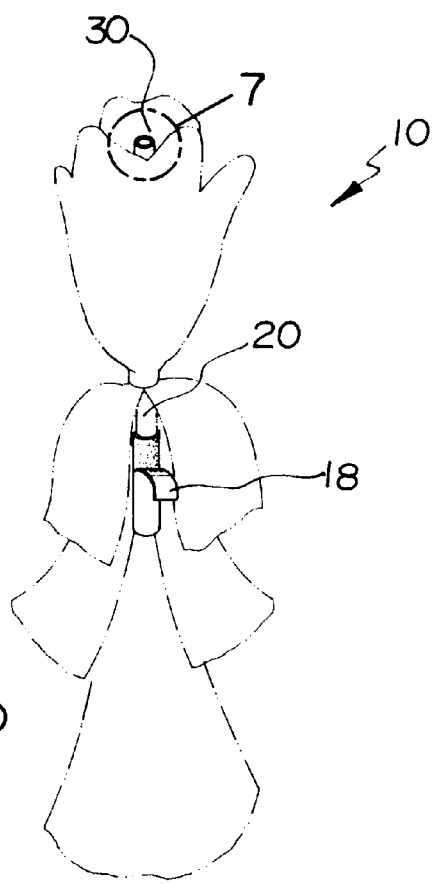
FIG. 5 is a cross-sectional breakaway view of the present invention taken from Line 5-5 of FIG. 4 illustrating an optional placement of a porous strip.
Figure 6:
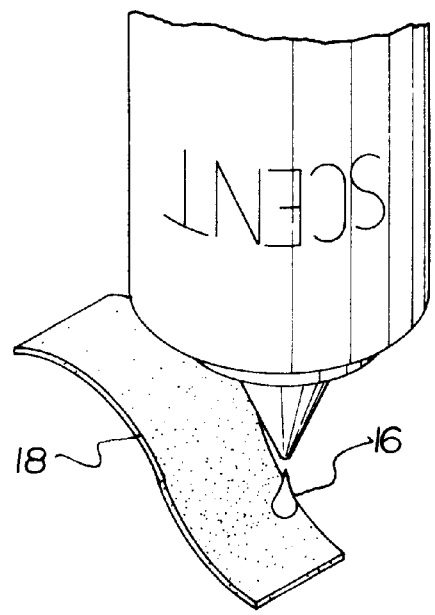
FIG. 6 is a detailed view particularly illustrating the application of a scent emitting liquid to a porous strip.

The first stem member 20 has upper and lower ends 22,24 and an interior. Preferably, the first stem member 20 is generally cylindrical. Also preferably, as shown in FIG. 2, the first end 42 of the first fringe member 40 is wrapped around the first stem member 20 between the ends 22,24 of the first stem member 20.

The second stem member 30 is removably insertable into the first stem member 20. Preferably, the second stem member 30 is generally cylindrical.

The first fringe member 40 has a first end 42, a second end 44, and a plurality of strips 46 that extend from the second end 44 towards the first end 42 such that the strips 46 are connected together at the first end 42 of the first fringe member 40. The first fringe member 40 may be produced from a sheet of white or colored paper or other material such as felt. The strips 46 of the first fringe member 40 may be colored to produce any desired design.

The second fringe member 50 has a first end 52, a second end 54, an attachment portion 56 that is positioned between the first and second ends 52,54 of the second fringe member 50, and a plurality of first and second strips 58,59. The first strips 58 of the second fringe member 50 extend from the first end 52 of the second fringe member 50 towards the attachment portion 56 of the second fringe member 50 such that the first strips 58 are coupled together at the attachment portion 56 of the second fringe member 50. The second strips 59 of the second fringe member 50 extend from the second end 54 of the second fringe member 50 towards the attachment portion 56 of the second fringe member 50 such that the second strips 59 are coupled together at the attachment portion 56 of the second fringe member 50.

The second fringe member 50 may likewise be produced from a sheet of white or colored paper or other material such as felt. The first and second strips 58,59 of the second fringe member 50 may be colored to produce any desired design.

Preferably, the second fringe member 50 has a length that extends between the first and second ends 52,54 of the second fringe member 50. The attachment portion 56 of the second fringe member 50 is positioned between the ends 52,54 of the second fringe member 50 at about one-third of the length of the second fringe member 50 from the first end 52 of the second fringe member 50.

Also preferably, the attachment portion 56 of the second fringe member 50 is wrapped around the first stem member 20. Ideally, the attachment portion 56 of the second fringe member 50 is coupled to the first stem member 20 at a position between the first fringe member 40 and the upper end 22 of the first stem member 20.

A plurality of leaf members 60 are provided. Each leaf member 60 has a leaf-shaped portion 62 that extends from an elongate attachment portion 64.

Preferably, each of the attachment portions 64 of the leaf members 60 is wrapped around the first stem member 20. Ideally, the attachment portions 64 of each of the leaf members 60 is coupled to the first stem member 20 at a position between the second fringe member 50 and the upper end 22 of the first stem member 20.

The third fringe member 70 has a first end 72, a second end 74, and a plurality of strips 76 that extends from the second end 74 of the third fringe member 70 towards the first end 72 of the third fringe member 70 such that the strips 76 are coupled together at the first end 72 of the third fringe member 70.

Preferably, the first end 72 of the third fringe member 70 is wrapped around the first stem member 20. Ideally, the first end 72 of the third fringe member 70 is coupled to the first stem member 20 at a position between the leaf members 60 and the upper end 22 of the first stem member 20

Figure 7:
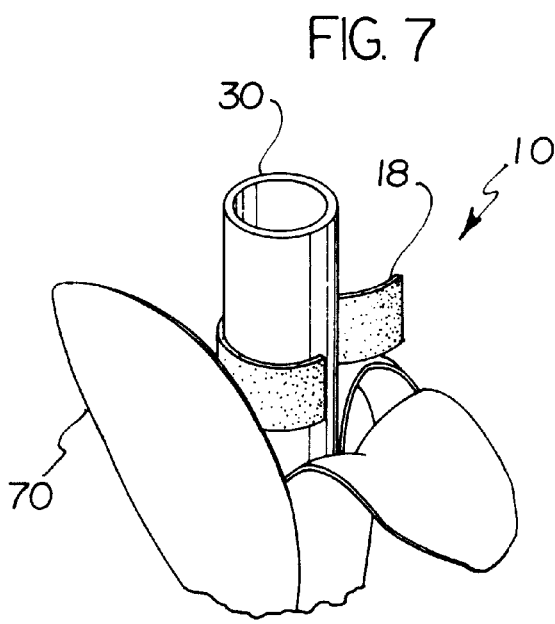
FIG. 7 is a detailed view of the present invention taken from Circle 7 of FIG. 5 particularly illustrating wrapping of a porous strip around a stem member

A scent emitting liquid 16 and a porous strip 18 that receives the scent emitting liquid 16 are provided. Preferably, as shown in FIG. 7, the porous strip 18 is coupled to the second stem member 30. The second stem member 30 and porous strip 18 coupled to it may be removed. A new stem member with another scented porous strip coupled to it may be inserted into the first stem member 20.

Preferably, an adhesive 14 couples the porous strip 18 to the second stem member 30.

In use, one method for producing scent emitting artificial flower type articles comprises the steps of forming an elongate stem member 20 that has upper and lower ends 22,24.

Preferably, the stem member 20 is created by distributing a portion of the adhesive 14 along a first end of a first sheet (not shown) of paper or other desired material and rolling up the first sheet from a first end of the first sheet towards a second end of the first sheet such that the adhesive 14 on the first end of the first sheet attaches to the first sheet at a portion of the first sheet that is spaced apart from the first end of the first sheet.

Also preferably, the stem member 20 has an interior. In such an embodiment, an elongate second stem member 30 may be created. The second stem member 30 is removably insertable into the interior of the first stem member 20 such that it may be replaced as set forth above.

The second stem member 30 may be created by distributing a portion of the adhesive 14 along a first end of a second sheet (not shown) and rolling up the second sheet from a first end of the second sheet towards a second end of the second sheet such that the adhesive 14 on the first end of the second sheet attaches to the second sheet at a portion of the second sheet that is spaced apart from the first end of the second sheet.

A first fringe member 40 with first and second ends 42,44, an attachment portion 48 that is positioned adjacent the first end 42, and a plurality of strips 46 that extend from the second end 44 of the first fringe member 40 to the attachment portion 48 of the first fringe member 40 is created. The strips 46 are connected to the first end 42 by the attachment portion 48 of the first fringe member 40.

Preferably, the first fringe member 40 is created from a third sheet (not shown) that is cut from a second end of the third sheet towards an attachment portion of the third sheet to form a plurality of strips that extend from the second end of the third sheet. The strips are connected to a first end of the third sheet by the attachment portion of the third sheet.

The attachment portion of the first fringe member 40 is wrapped around the stem member 20. Preferably, a portion of the adhesive 14 is applied such that the adhesive 14 attaches the attachment portion 48 of the first fringe member 40 to the stem member 20.

A second fringe member 50 with first and second ends 52,54, a length that extends between the first end 52 and the second end 54, an attachment portion 56 that is positioned less than about one-third of the length from the first end 52, a plurality of first strips 58 that extend from the first end 52 of the second fringe member 50 to the attachment portion 56 of the second fringe member 50, and a plurality of second strips 59 that extend from the second end 54 of the second fringe member 50 to the attachment portion 56 of the second fringe member 50 is created.

Preferably, the second fringe member 50 is formed by cutting a fourth sheet (not shown) to form a plurality of first strips that extend from a first end of the fourth sheet towards an attachment portion of the fourth sheet and cutting the fourth sheet to form a plurality of second strips that extend from a second end of the fourth sheet towards the attachment portion of the fourth sheet.

The attachment portion 56 of the second fringe member 50 is wrapped around the stem member 20. Preferably, the attachment portion 56 of the second fringe member 50 is wrapped around the stem member 20 between the first fringe member 40 and the upper end 22 of the stem member 20. Also preferably, a portion of the adhesive 14 is applied such that the adhesive 14 attaches the attachment portion 56 of the second fringe member 50 to the stem member 20.

A plurality of leaf members 60 are formed. Each leaf member 60 has a leaf-shaped portion 62 that extends from an elongate attachment portion 64.

Preferably, the leaf members 60 are created by folding a fifth sheet (not shown) such that the creases formed by folding the fifth sheet define four equal portions of the fifth sheet. The fifth sheet is cut along the creases to separate the portions of the fifth sheet. Each of the portions of the fifth sheet are cut to form a generally leaf shaped pattern with a leaf-shaped portion that extends from an elongate attachment portion.

The attachment portion 64 of each of the leaf members 60 is wrapped around the stem member 20. Preferably, the attachment portion 64 of each of the leaf members 60 is wrapped around the stem member 20 between the second fringe member 50 and the upper end 22 of the stem member 20. Also preferably, a portion of the adhesive 14 is applied such that the adhesive 14 attaches each of the attachment portions 64 of the leaf members 60 to the stem member 20.

A third fringe member 70 with first and second ends 72,74, an attachment portion 78 that is positioned adjacent the first end 72, and a plurality of strips 76 that extend from the second end 74 of the third fringe member 70 to the attachment portion 78 of the third fringe member 70 is formed. The strips 76 are connected to the first end 72 of the third fringe member 70 by the attachment portion 78 of the third fringe member 70.

Preferably, the third fringe member 70 is created by cutting a sixth sheet (not shown) from a second end of the sixth sheet towards an attachment portion at a first end of the sixth sheet to form a plurality of strips that extend from the attachment portion of the third sheet.

The attachment portion 78 of the third fringe member 70 is wrapped around the stem member 20. Preferably, the attachment portion of the third fringe member 70 is wrapped around the stem member 20 between the leaf members 60 and the upper end 22 of the stem member 20. Also preferably, a portion of the adhesive 14 is applied such that the adhesive 14 attaches the attachment portion 78 of the third fringe member 70 to the stem member 20.

A porous strip 18 is wrapped around the stem member 20 towards the upper end 22 of the stem member 20. Preferably, the adhesive 14 is applied such that the adhesive 14 attaches the porous strip 18 to the stem member 20. Alternatively, the porous strip 18 may be wrapped around the second stem member 30.

A scent emitting liquid 16 is provided. A portion of the scent emitting liquid 16 is applied to the porous strip 18.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A kit for producing scent emitting artificial flower articles, said kit comprising:
    an elongate first stem member having upper and lower ends and an interior;
    an elongate second stem member, said second stem member being insertable into said first stem member;
    a first fringe member having a first end, a second end, and a plurality of strips extending from said second end towards said first end of said first fringe member such that said strips are connected together at said first end of said first fringe member;
    a second fringe member having a first end, a second end, an attachment portion being positioned between said first and second ends of said second fringe member, and a plurality of first and second strips;
    wherein said first strips extend from said first end of said second fringe member towards said attachment portion of said second fringe member such that said first strips are coupled together at said attachment portion of said second fringe member;
    wherein said second strips extend from said second end of said second fringe member towards said attachment portion of said second fringe member such that said second strips are coupled together at said attachment portion of said second fringe member;
    a plurality of leaf members each having a leaf-shaped portion extending from an elongate attachment portion;
    a third fringe member having a first end, a second end, and a plurality of strips extending from said second end of said third fringe member towards said first end of said third fringe member such that said strips are coupled together at said first end of said third fringe member;
    a scent emitting liquid; and
    a porous strip for receiving said scent emitting liquid.

2. The kit of claim 1, wherein said first end of said first fringe member is wrapped around said first stem member between said ends of said first stem member.

3. The kit of claim 1, wherein said second fringe member has a length extending between said first and second ends of said second fringe member, wherein said attachment portion of said second fringe member is positioned between said first and second ends of said second fringe member at about one-third of said length from said first end of said second fringe member.

4. The kit of claim 2, wherein said attachment portion of said second fringe member is wrapped around said first stem member.

5. The kit of claim 4, wherein said attachment portion of said second fringe member is coupled to said first stem member at a position between said first fringe member and said upper end of said first stem member.

6. The kit of claim 5, wherein each of said attachment portions of said leaf members is wrapped around said first stem member.

7. The kit of claim 6, wherein said attachment portions of each of said leaf members is coupled to said first stem member at a position between said second fringe member and said upper end of said first stem member.

8. The kit of claim 7, wherein said first end of said third fringe member is wrapped around said first stem member, said first end of said third fringe member being coupled to said first stem member at a position between said leaf members and said upper end of said first stem member.

9. The kit of claim 8, wherein an adhesive couples said porous strip to said second stem member.

10. A kit for producing scent emitting artificial flower articles, said kit comprising:
    an elongate first stem member being generally cylindrical and having upper and lower ends and an interior;
    an elongate second stem member being generally cylindrical, said second stem member being insertable into said first stem member;
    a first fringe member having a first end, a second end, and a plurality of strips extending from said second end towards said first end of said first fringe member such that said strips are connected together at said first end of said first fringe member;

wherein said first end of said first fringe member is wrapped around said first stem member between said ends of said first stem member;

a second fringe member having a first end, a second end, a length extending between said first and second ends of said second fringe member, an attachment portion being positioned between said first and second ends of said second fringe member at about one-third of said length from said first end of said second fringe member, and a plurality of first and second strips;

wherein said first strips extend from said first end of said second fringe member towards said attachment portion of said second fringe member such that said first strips are coupled together at said attachment portion of said second fringe member;

wherein said second strips extend from said second end of said second fringe member towards said attachment portion of said second fringe member such that said second strips are coupled together at said attachment portion of said second fringe member;

wherein said attachment portion of said second fringe member is wrapped around said first stem member;

wherein said attachment portion of said second fringe member is coupled to said first stem member at a position between said first fringe member and said upper end of said first stem member;

a plurality of leaf members each having a leaf-shaped portion extending from an elongate attachment portion;

wherein each of said attachment portions of said leaf members is wrapped around said first stem member, said attachment portions of each of said leaf members being coupled to said first stem member at a position between said second fringe member and said upper end of said first stem member;

a third fringe member having a first end, a second end, and a plurality of strips extending from said second end towards said first end of said third fringe member such that said strips are coupled together at said first end of said third fringe member;

wherein said first end of said third fringe member is wrapped around said first stem member, said first end of said third fringe member being coupled to said first stem member at a position between said leaf members and said upper end of said first stem member;

a scent emitting liquid; and a porous strip for receiving said scent emitting liquid, wherein an adhesive couples said porous strip to said second stem member.

\* \* \* \* \*